United States Patent

Buonomo et al.

[11] Patent Number: 6,031,143
[45] Date of Patent: Feb. 29, 2000

[54] PROCESS FOR THE PRODUCTION OF STYRENE

[75] Inventors: Franco Buonomo, S. Donato Milanese; Gianni Donati, Rho; Emilio Micheli, Milan; Lorenzo Tagliabue, Cusano Milanino, all of Italy

[73] Assignee: Snamprogetti S.p.A., S. Donato Milanese, Italy

[21] Appl. No.: 09/144,986

[22] Filed: Sep. 1, 1998

[30] Foreign Application Priority Data

Sep. 26, 1997 [IT] Italy ................ MI97/A2175

[51] Int. Cl.[7] .............. C07C 1/00; C07C 4/02; C07C 2/64; C07C 5/333
[52] U.S. Cl. ............. 585/323; 585/315; 585/316; 585/441; 585/444; 585/445; 585/600; 585/661; 585/662; 585/663
[58] Field of Search ................ 585/323, 315, 585/316, 441, 444, 445, 660, 661, 662, 663

[56] References Cited

U.S. PATENT DOCUMENTS

| | | | |
|---|---|---|---|
| 2,376,532 | 5/1945 | Egloff | 260/669 |
| 5,143,886 | 9/1992 | Iezzi et al. | 502/242 |
| 5,254,787 | 10/1993 | Dessau | 585/654 |
| 5,308,822 | 5/1994 | Iezzi et al. | 502/243 |
| 5,414,182 | 5/1995 | Iezzi et al. | 585/661 |

FOREIGN PATENT DOCUMENTS 0 637 578  2/1985  European Pat. Off. .

*Primary Examiner*—Walter D. Griffin
*Assistant Examiner*—Thuan D. Dang
*Attorney, Agent, or Firm*—Oblon, Spivak, McClelland, Maier & Neustadt, P.C.

[57] ABSTRACT

Process for the production of styrene which comprises:
a) feeding to an alkylation unit a stream of benzene and a stream of recycled product containing ethylene;
b) mixing the stream at the outlet of the alkylation unit, containing ethylbenzene, with a stream consisting of ethane;
c) feeding the mixture thus obtained to a dehydrogenation unit containing a catalyst capable of contemporaneously dehydrogenating ethane and ethylbenzene;
d) feeding the product leaving the dehydrogenation unit to a separation section to produce a stream essentially consisting of styrene and a stream containing ethylene;
e) recycling the stream containing ethylene to the alkylation unit.

21 Claims, 1 Drawing Sheet

PROCESS FOR THE PRODUCTION OF STYRENE

BACKGROUND OF THE INVENTION

1. Field of the Invention

The present invention relates to a process for the production of styrene.

More specifically, the present invention relates to a process for the production of styrene starting from benzene and ethane.

Even more specifically, the present invention relates to a process for the production of styrene by the simultaneous dehydrogenation of ethylbenzene and ethane to give styrene and ethylene respectively.

2. Description of the Background

As is well known, styrene is a product which is used in the production of thermoplastic polymers, such as polystyrenes (PS), acrylonitrile-butadiene-styrene copolymers (ABS), styrene-acrylonitrile resins (SAN), styrene-butadiene elastomeric copolymers (SBR) and in formulations for unsaturated polyester resins.

Styrene is generally prepared by the adiabatic or isothermic catalytic dehydrogenation of ethylbenzene in the presence of catalysts selected from metal oxides or their mixtures. In published international patent application WO97-18034, for example, the catalyst consists of a mixture comprising $Fe_2O_3$, $K_2O$, $MnO_3$, MgO, at least one oxide of Cu, Zn, Sc, Ti, W, Mn, Ni, Pd, Al, P, Bi, B, Sn, Pb and Si and at least two rare-earth metals. In Italian patent application MI97A-1463, on the other hand, the catalyst consists of a mixture of $Cr_2O_3$, SnO and at least one alkaline oxide supported on alumina in delta or theta phase. Further information on the dehydrogenation of ethylbenzene is available in Stanford Research Institute (SRI International) Report 338, 1977.

Ethylbenzene is, in turn, prepared by the alkylation of benzene, available as a refinery product, with ethylene coming from the cracking or dehydrogenation of ethane. The alkylation reaction can be carried out in vapour phase, using as catalysts zeolites with high $SiO_2/Al_2O_3$ ratios, for example zeolites of the type ZSM-5 or Lewis acids, or in liquid phase. Details on the alkylation of benzene with ethylene are available in SRI.

The tradional methods for the production of styrene therefore generally require the availability of ethylene for the preparation of ethylbenzene.

SUMMARY OF THE INVENTION

With the aim of simplifying traditional production processes, the Applicant has now found a new method for the preparation of styrene in which ethylene and styrene are contemporaneously produced in the same dehydrogenation unit.

The present invention therefore relates to a process for the production of styrene which comprises:

a) feeding to an alkylation unit a stream of benzene and a stream of recycled product containing ethylene;
b) mixing the stream at the outlet of the alkylation unit, containing ethylbenzene, with a stream consisting of ethane;
c) feeding the mixture thus obtained to a dehydrogenation unit containing a catalyst capable of contemporaneously dehydrogenating ethane and ethylbenzene to give ethylene and styrene respectively;
d) feeding the product leaving the dehydrogenation unit to a separation section to produce a stream essentially consisting of styrene and a stream containing ethylene;
e) recycling the stream containing ethylene to the alkylation unit.

DETAILED DESCRIPTION OF THE INVENTION

Figure 1:
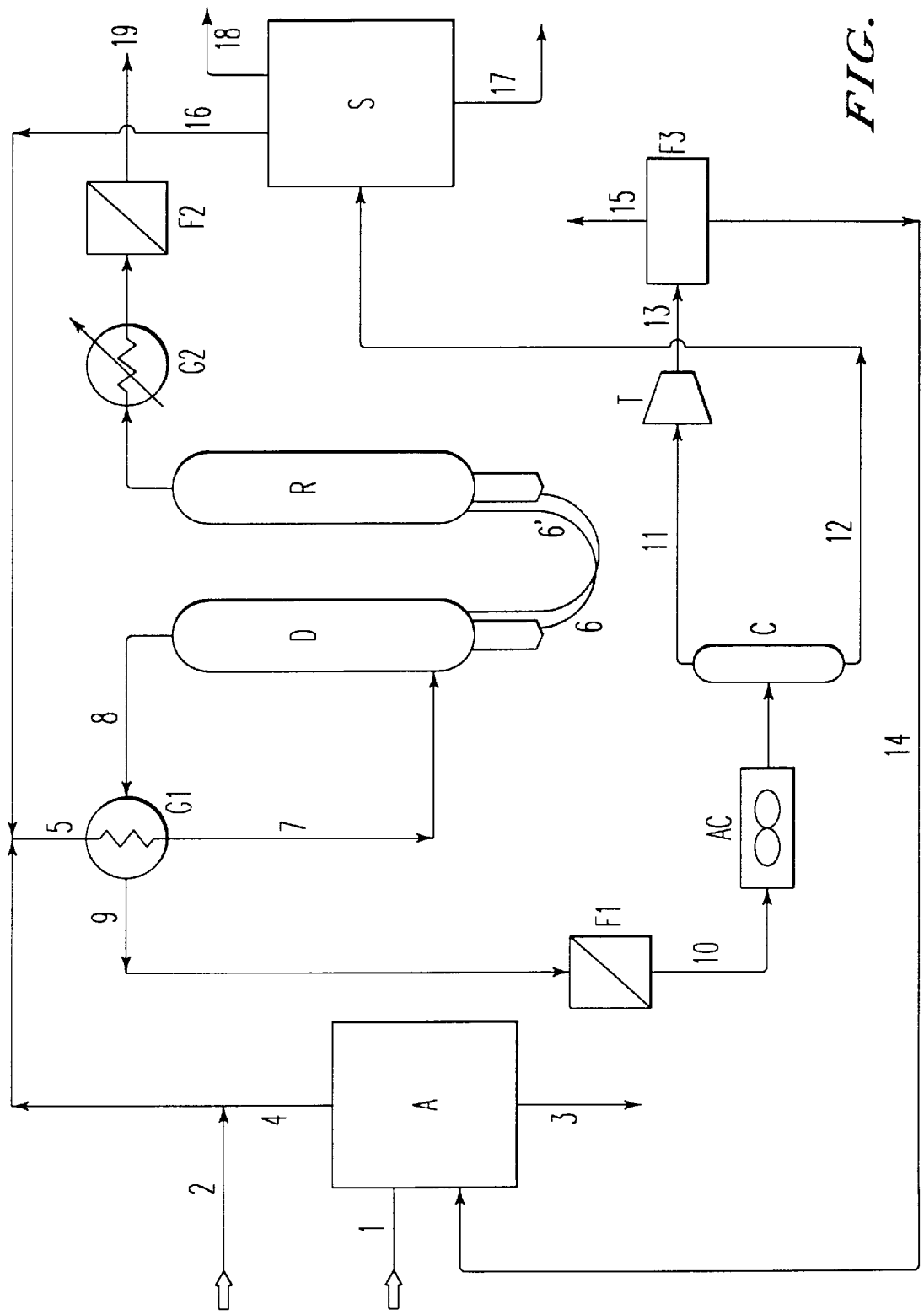
FIG. 1 is a block diagram detailing the presently-disclosed process.

According to the present invention, a first stream of fresh loading of benzene, refinery grade, consequently with a purity of more than 95% by weight, is fed to the alkylation unit, together with a second stream of recycled product, essentially consisting of ethylene and non-converted ethane. More specifically, this second stream consists of 2–50% by weight of ethylene; 50–98% by weight of ethane.

In the recycled stream 0.1–1% by weight (calculated out of the total of ethylene+ethane) of other light products, formed in both the alkylation and dehydrogenation phase, are also present.

The two streams are fed to the alkylation unit so as to have benzene/ethylene ratios required by current technologies which are typically between 3 and 10.

The alkylation reaction is carried out with conventional systems, for example according to the method described in published European patent application 432.814.

The ethane mixed with the alkylation product is a stream of fresh loading coming from the refinery and is therefore available, like benzene, with a purity higher than or equal to 95% by weight. To obtain a good balance between the alkylation and dehydrogenation reactions it is preferable for the total ethane, both recycled and in the feeding, to be present in the alkylated stream so as to have molar ratios ethylbenzene/ethane preferably of between 0.01 and 1.

The mixture obtained, after the addition of ethane and possibly recycled ethylbenzene, is fed to the dehydrogenation unit which mainly consists of a reaction reactor and a regeneration reactor of the catalyst.

The dehydrogenation reaction is carried out in gaseous phase operating in fixed-bed or fluid-bed catalytic reactors, even if fluid-bed reactors are preferred for their technological advantages which are well known to experts in the field.

Any catalyst capable of contemporaneously dehydrogenating a paraffin such as ethane and an alkylaromatic hydrocarbon such as ethylbenzene can be used in the process of the present invention.

For example, a catalyst which is particularly suitable for this type of reaction is based on gallium and platinum on alumina in delta or theta phase or in a mixture of delta+theta, theta+alpha or delta+theta+alpha phases, modified with silica, and having a surface area preferably less than 100 $m^2/g$, determined with the BET method.

More specifically it is a catalyst which comprises:

i) 0.1–34% by weight, preferably 0.2–3.8%, of $Ga_2O_3$;
ii) 1–99 ppm (by weight), preferably 3–80 ppm, of platinum;
iii) 0.05–5% by weight, preferably 0.1–3%, of an alkaline and/or earth-alkaline oxide, for example potassium;
iv) 0.08–3% by weight of silica; the complement to 100 being alumina.

A process for preparing the catalyst described above essentially consists in dispersing the precursors of the metals onto a carrier consisting of alumina and silica.

An example of dispersion can comprise the impregnation of the carrier with a solution containing the precursors of gallium and platinum followed by drying and calcination. An alternative method consists in ion absorption, followed by the separation of the liquid, drying and activation of the solid or surface adsorption of volatile species of gallium and platinum and possible calcination of the solid.

Among the procedures listed above impregnation or immersion of the carrier in the solution containing the precursors is preferred.

In the case of alkaline or earth-alkaline metal, the addition procedures consist in:

coimpregnation of the carrier;

addition of the metal to the carrier before the dispersion of the precursor of gallium and platinum;

treatment of the solid containing gallium and platinum by ion exchange, impregnation, etc. with the alkaline or earth-alkaline metal.

Another catalyst which can be used in the process of the present invention is described in Italian patent application MI97A-1463 and consists of:

i) 6–30% by weight, preferably 13–25%, of $Cr_2O_3$;
ii) 0.1–3.5% by weight, preferably 0.2–2.8%, of SnO;
iii) 0.4–3% by weight, preferably 0.5–2.5%, of an alkaline oxide, for example potassium;
iv) 0.08–3% by weight of silica; the complement to 100 being alumina in delta or theta phase or in a mixture of delta+theta, theta+alpha or delta+theta+alpha phases.

The dehydrogenation reaction is carried out at a temperature ranging from 450 to 700° C., at a pressure ranging from 0.1 to 3 atms and with a flow-rate of the reagents, expressed as hourly volumetric flow-rate of the reagents per liter of catalyst (Gas Hourly Space Velocity or GHSV) ranging between 100 and 10,000 $h^{-1}$. The catalyst can be used as such or diluted with an inert product, for example alpha-alumina possibly modified with oxides of alkaline metals and/or silica, at a weight concentration of the inert product of between 0 and 50%.

In the fluid-bed dehydrogenation reactor, it is preferable to operate:

at a temperature ranging from 450 to 650° C.;
at a pressure which is atmospheric or slightly higher;
at a space velocity of between 100 and 1000 $h^{-1}$, preferably between 150 and 300 $h^{-1}$;

with a residence time of the catalyst in the fluid-bed zone varying from 5 to 30 minutes, preferably from 10 to 15 minutes and in the desorption zone from 0.2 to 10 minutes.

During the dehydrogenation reaction, the catalytic system (catalyst+possible diluent) is continuously removed from the reactor to be regenerated.

In the regenerator it is preferable to operate at a pressure which is atmospheric or slightly higher, at a space velocity ranging from 100 to 1000 $h^{-1}$ and with a residence time of the solid varying from 5 to 60 minutes or from 20 to 40 minutes. The regeneration temperature is generally between 600 and 700° C.

The regenerated catalyst is transported to the reactor in the same way in which the exhausted catalyst is transported to the regenerator. The regenerator reactor system thus conceived enables the operating parameters and performances of the process to be kept constant.

The regenerated catalytic system is continuously readmitted to the dehydrogenation reactor so that the heat necessary for the reaction is removed from the regenerated catalyst which is refed at a temperature which is higher than the average reaction temperature.

Before being readmitted to the dehydrogenation reactor, the catalyst can optionally be subjected to reducing treatment, at temperatures ranging from 650 to 700° C. in the presence of a reducing agent, for example methane, for times ranging from 0.2 to 10 minutes.

At the end of the dehydrogeneration reaction, a dehydrogenated stream is recovered, essentially consisting in ethylene and styrene. More specifically, the stream comprises: 2–35% by weight of styrene; 1–20% of ethylene; 25–75% of non-reacted ethane and 2–40% of non-reacted ethylbenzene; 0.1–2% of other products such as methane, hydrogen, toluene, benzene formed during both the alkylation and dehydrogenation reaction.

The dehydrogenated stream is cooled, filtered and sent to a distillation section for the recovery of the styrene and non-reacted ethylbenzene, which is recycled to the dehydrogenation, and the recovery of the stream containing ethylene, which is recycled as feeding to the alkylation unit.

The process for the production of styrene of the present invention can be more easily understood by referring to the block diagram of the enclosed FIGURE which represents an illustrative but non-limiting embodiment.

With reference to the diagram, (A) represents the alkylation unit, (D) the dehydrogenation reactor, (R) the regeneration unit of the catalyst, (C) a separator, (S) a distillation system and (F1), (F2) and (F3) are three filtration units. (G1) and (G2) represent two heat exchangers, (AC) is an air cooler and (T) a compression unit.

The present process can therefore be clearly understood from the enclosed diagram and previous description. In fact, a stream (1) consisting of benzene and a stream (14), of recycled products, essentially consisting of ethylene and ethane, as well as traces of methane and hydrogen are fed, as reagents, to the alkylation unit (A). The inert products (3) which would otherwise accumulate in the productive cycle are separated from the alkylation unit.

The stream of alkylated product (4), essentially consisting of ethylbenzene and ethane, is mixed with a stream (2) consisting of ethane and with a stream of recycled ethylbenzene (16). The mix (5) thus obtained, after pre-heating in (G1), is fed (7) to the dehydrogenation reactor (D). The reactor (D) operates in combination with the regenerating unit of the catalyst (R). In particular, small portions of catalyst are continuously removed from the reactor (D) and transferred, by line (6), to the regenerator (R). Contemporaneously, analogous portions of regenerated catalyst are removed from the regenerator (R) and readmitted to the reactor (D) by line (6'). The effluent gases (19) from the regenerator (R) are cooled in (G2), filtered in (F2) and discharged.

The dehyrogenated product (8), which essentially consists of styrene, non-reacted ethylbenzene and ethane, methane and hydrogen and other products such as toluene and benzene, is cooled in (G1), filtered in (F1), cooled in the air cooler (AC) and fed to the separator (C).

A stream (12) of condensable products, essentially consisting of styrene, ethylbenzene and other by-products (benzene, toluene), is recovered from the bottom of (C). A stream (11) of light products essentially consisting of ethylene, ethane, methane and hydrogen, is recovered from the head of (C).

The stream (12) goes to the distillation unit (S), for example to a unit comprising one or more distillation columns, from which the styrene (18) with a high degree of purity (>99.5%), is recovered together with the ethylbenzene (16) which is recycled to the dehydrogenation and the by-products (17) which go to subsequent treatments.

The stream (11) is brought to the operating pressure of the alkylation unit in (T), separated from the hydrogen (15) in the membrane filter (F3) and recycled in (A), as primary feeding, by means of line (14).

An illustrative but non-limiting example is provided for a better understanding of the present invention and for its embodiment.

EXAMPLE 1

Preparation of the dehydrogenation catalyst

A microspheroidal pseudobohemite is prepared to which silica has been added (1.2% w), with a particle diameter of between 5 and 300 microns, by spray-drying a hydrated alumina sol and Ludox silica.

A sample of the pseudobohemite is subjected to thermal treatment consisting in a first calcination at 450° C. for 1 hour, followed by a second calcination at 1180° C. of 4 hours in a stream of dry air.

The product obtained has a specific surface of 32 $m^2/g$, a porosity of 0.22 $cm^3/g$ and prevalently consists of alpha-alumina, accompanied by delta and theta transition aluminas.

200 g of this alumina were impregnated, using the incipient wetness procedure, with 44 $cm^3$ of an aqueous solution containing: 14.85 gr of $Ga(NO_3)_3$, 1.78 g of $KNO_3$ and 6 $cm^3$ of an aqueous solution of $Pt(NH_3)_2(HCO_3)_2$ so as to have a concentration of Pt equal to 2.5 g/l.

The impregnation is carried out at room temperature. The impregnated product is left to rest for 1 hour at room temperature in a stream of dry air and subsequently dried at 90° C. for 15 hours. The dried product is finally treated in a fluid bed for 4 hours at 750° C. in a stream of dry air.

The weight composition of the formulate thus obtained proves to be as follows: 2.33% $Ga_2O_3$, 0.4% $K_2O$, 75 ppm Pt, 1.56% $SiO_2$, $Al_2O_3$ the complement to 100.

EXAMPLES 2–4

101 g of the catalyst of example 1 were charged into a quartz reactor having an internal diameter of 25 mm. The reactor is heated by means of an electric oven to maintain the catalytic bed at the desired temperature.

The ethylbenzene is fed to an evaporator by means of a dosage pump and then mixed with a stream of ethane whose flow-rate is measured by a rotameter.

The reaction mixture is preheated to 200° C. and fed to the reactor from the bottom through a calibrated septum which operates as a gas distributor thus fluidizing the catalyst. An expansion vase is assembled on the head of the reactor with the function of decelerating the effluent gas and allowing the fine particles of catalyst to fall back into the reactor. The expander and sampling lines are maintained at a temperature of 200° C. to avoid the condensation of styrene, non-reacted ethylbenzene and possible heavy by-products.

The effluent from the reactor is sent into a condenser cooled with dry ice whereas the non-condensable products are collected in a bag connected down-stream.

At the end of the reaction, the condenser is slowly brought to room temperature and the liquid product is collected and analyzed.

The reaction phase is followed by the regeneration phase in which the coke which is deposited on the catalyst is burnt by feeding air to the reactor for 45 minutes at a temperature of 660° C. The effluent from the reactor is collected in a bag.

The enclosed table shows the operating parameters and results obtained.

Analyses of the condensed reaction products were carried out via gas-chromatography with an HP 5890 instrument equipped with a flame ionization detector (FID). A CP-WAX 10 capillary column (50 m) was used for the separation of the components of the mixture.

The gases collected during the reaction and regeneration step are analyzed with an HP 5890 gas-chromatograph equipped with a thermoconductivity detector (TCD) and an analytical system for the separation of hydrogen, nitrogen, oxygen, CO, $CO_2$, methane, ethane, ethylene. The dosing of the different species is carried out with the standard external method.

EXAMPLE 5

With reference to the diagram of FIG. 1, 1 Kg/h of benzene is fed (1) to the alkylation unit (A) together with the recycled stream (14) having a flow-rate of 4.2 Kg/h and containing 8.3% by weight of ethylene.

The alkylation reaction is carried out at a pressure of 40 atms and at a temperature of 180° C. according to what is described in published European patent 432.814.

The stream (4), coming from the alkylation, contains 26% by weight of ethylbenzene, 73.5% of ethane as well as hydrogen and methane. The overall flow-rate is 5.2 Kg/h. To this are added the stream of ethane (2), 0.44 Kg/h, and the recycled stream of ethylbenzene (16), 1.5 Kg/h, obtaining the stream (7) which forms the feeding to the dehydrogenation reactor.

The dehydrogenation reaction is carried out at a temperature of 600° C. and at an average pressure of 1.1 atms.

The effluent stream from the reactor (8) contains 17.8% by weight of styrene and 5% by weight of ethylene. After cooling, the stream (8) is separated into a first stream essentially containing styrene and ethylbenzene (12) and a second stream (11) which contains the gaseous phase. The hydrogen (15) is separated from the latter, by means of the membrane system F3, obtaining the stream (14).

The stream (12) is sent to the distillation system (S) from which the stream (18) consisting of styrene, the stream (16) essentially containing non-reacted ethylbenzene and the stream (17) consisting of dehydrogenation by-products, in particular benzene and toluene, are recovered.

TABLE 1

| Example | EB v/v % | $C_2H_6$ v/v % | Temp. ° C. | Press. Ate | WHSV EB Kg/h/Kg | SV $h^{-1}$ | EB conver. % | Etane conver. % | Styrene mol. sel. % | Ethylene mol. sel. % | Styrene g/h/Kg cat. | Ethylene g/h/Kg cat. | Ethylene/ Styrene mol/mol |
|---|---|---|---|---|---|---|---|---|---|---|---|---|---|
| 2 | 9 | 91 | 600 | 1.1 | 0.20 | 587 | 57.9 | 12 | 94.0 | 95 | 105 | 60 | 2.12 |
| 3 | 19.1 | 80.9 | 600 | 1.1 | 0.43 | 596 | 50.0 | 8.5 | 94.0 | 95 | 196 | 38 | 0.73 |
| 4 | 28.8 | 71.2 | 600 | 1.1 | 0.64 | 595 | 45.4 | 7.1 | 94.1 | 95 | 267 | 28 | 0.39 |

We claim:

1. A process for the production of styrene which comprises:
   a) feeding to an alkylation unit a stream of benzene and a stream of recycled product containing ethylene;
   b) mixing the stream at the outlet of the alkylation unit, containing ethylbenzene, with a stream containing ethane;
   c) feeding the mixture thus obtained to a dehydrogenation unit containing a dehydrogenation catalyst capable of contemporaneously dehydrogenating ethane and ethylbenzene to give a product containing ethylene and styrene respectively;
   d) feeding the product leaving the dehydrogenation unit to a separation section to produce a stream containing styrene and a stream containing ethylene;
   e) recycling the stream containing ethylene to the alkylation unit,
   wherein the dehydrogenation catalyst comprises gallium and platinum supported on alumina modified with silica, and in the following amounts:
      i) 0.1–34% by weight, of $Ga_2O_3$;
      ii) 1–99 ppm by weight of platinum;
      iii) 0.05–5% by weight of an alkaline and/or earth-alkaline oxide;
      iv) 0.08–3% by weight of silica;
   the remainder being alumina, wherein said alumina is in delta or theta phase or in a mixture of delta+theta, theta+alpha or delta+theta+alpha phases, modified with silica, and wherein the catalyst has a surface area of less than 100 $m^2/g$, determined by means of the BET method.

2. The process according to claim 1, wherein the recycled stream consists essentially of 2–50% by weight of ethylene and 50–98% by weight of ethane.

3. The process according to claim 2, wherein
   i) $Ga_2O_3$ is present in an amount of 0.2–3.8% by weight;
   ii) platinum is present in an amount of 3–80 ppm by weight;
   iii) alkaline and/or earth-alkaline oxide is present in an amount of 0.1–3% by weight.

4. The process according to claim 1 or 2, wherein ethylbenzene and ethane are fed to the dehydrogenation unit in molar ratios ethylbenzene/ethane ranging between 0.01 and 1.

5. The process according to claim 4, wherein
   i) $Ga_2O_3$ is present in an amount of 0.2–3.8% by weight;
   ii) platinum is present in an amount of 3–80 ppm by weight;
   iii) alkaline and/or earth-alkaline oxide is present in an amount of 0.1–3% by weight.

6. The process according to claim 1, wherein the dehydrogenation reaction takes place at a temperature ranging from 450 to 700° C., at a pressure ranging from 0.1 to 3 atms and with a flow-rate of reagents ethane and ethylbenzene, expressed as hourly volumetric flow-rate of the reagents per liter of catalyst (Gas Hourly Space Velocity or GHSV) of between 100 and 10,000 $h^{-1}$.

7. The process according to claim 1, wherein the dehydrogenation reaction is carried out in a fluid-bed reactor which operates:
   at a temperature ranging from 450 to 650° C.;
   at a pressure which is atmospheric or slightly higher;
   at a space velocity ranging between 100 and 1000 $h^{-1}$.

8. The process according to claim 7, wherein the space velocity ranges between 150 and 300 $h^{-1}$.

9. The process according to claim 1, wherein
   i) $Ga_2O_3$ is present in an amount of 0.2–3.8% by weight;
   ii) platinum is present in an amount of 3–80 ppm by weight;
   iii) alkaline and/or earth-alkaline oxide is present in an amount of 0.1–3% by weight.

10. A process for the production of styrene which comprises:
    a) feeding to an alkylation unit a stream of benzene and a stream of recycled product containing ethylene;
    b) mixing the stream at the outlet of the alkylation unit, containing ethylbenzene, with a stream containing ethane;
    c) feeding the mixture thus obtained to a dehydrogenation unit containing a dehydrogenation catalyst capable of contemporaneously dehydrogenating ethane and ethylbenzene to give a product containing ethylene and styrene respectively;
    d) feeding the product leaving the dehydrogenation unit to a separation section to produce a stream containing styrene and a stream containing ethylene;
    e) recycling the stream containing ethylene to the alkylation unit, wherein the dehydrogenation catalyst comprises:
       i) 6–30% by weight of $Cr_2O_3$;
       ii) 0.1–3.5% by weight of SnO;
       iii) 0.4–3% by weight of an alkaline oxide;
       iv) 0.08–3% by weight of silica;
       the remainder being alumina in delta or theta phase or in a mixture of delta+theta, theta+alpha or delta+theta+alpha phases.

11. The process according to claim 10, wherein the recycled stream consists essentially of 2–50% by weight of ethylene and 50–98% by weight of ethane.

12. The process according to claim 11, wherein ethylbenzene and ethane are fed to the dehydrogenation unit in molar ratios ethylbenzene/ethane ranging between 0.01 and 1.

13. The process according to claim 12, wherein
    i) $Cr_2O_3$ is present in an amount of 13–25% by weight;
    ii) SnO is present in an amount of 0.2–2.8% by weight;
    iii) alkaline oxide is present in an amount of 0.5–2.5% by weight.

14. The process according to claim 11, wherein
    i) $Cr_2O_3$ is present in an amount of 13–25% by weight;
    ii) SnO is present in an amount of 0.2–2.8% by weight;
    iii) alkaline oxide is present in an amount of 0.5–2.5% by weight.

15. The process according to claim 10, wherein ethylbenzene and ethane are fed to the dehydrogenation unit in molar ratios ethylbenzene/ethane ranging between 0.01 and 1.

16. The process according to claim 15, wherein
    i) $Cr_2O_3$ is present in an amount of 13–25% by weight;
    ii) SnO is present in an amount of 0.2–2.8% by weight;
    iii) alkaline oxide is present in an amount of 0.5–2.5% by weight.

17. The process according to claim 10, wherein
    i) $Cr_2O_3$ is present in an amount of 13–25% by weight;
    ii) SnO is present in an amount of 0.2–2.8% by weight;
    iii) alkaline oxide is present in an amount of 0.5–2.5% by weight.

18. A process for the contemporaneous dehydrogenation of ethane and ethylbenzene to produce ethylene and styrene respectively comprising carrying out the dehydrogenation reaction in the presence of a catalytic system comprising:

i) 0.1–34% by weight of $Ga_2O_3$;

ii) 1–99 ppm by weight, of platinum;

iii) 0.05–5% by weight of an alkaline and/or earth-alkaline oxide;

iv) 0.08–3% by weight of silica;

the remainder being alumina in delta or theta phase or in a mixture of delta+theta, theta+alpha or delta+theta+alpha phases.

19. The process according to claim 18, wherein i) $Ga_2O_3$ is present in an amount of 0.2–3.8% by weight;

ii) platinum is present in an amount of 3–80 ppm by weight;

iii) alkaline and/or earth-alkaline oxide is present in an amount of 0.1–3% by weight.

20. A process for the contemporaneous dehydrogenation of ethane and ethylbenzene to produce ethylene and styrene respectively comprising carrying out the dehydrogenation reaction in the presence of a catalytic system comprising:

i) 6–30% by weight of $Cr_2O_3$;

ii) 0.1–3.5% by weight of SnO;

iii) 0.4–3% by weight of an alkaline oxide;

iv) 0.08–3% by weight of silica;

the remainder being alumina in delta or theta phase or in a mixture of delta+theta, theta+alpha or delta+theta+alpha phases.

21. The process according to claim 20, wherein i) $Cr_2O_3$ is present in an amount of 13–25% by weight;

ii) SnO is present in an amount of 0.2–2.8% by weight;

iii) alkaline oxide is present in an amount of 0.5–2.5% by weight.

* * * * *